United States Patent [19]
Yoon

[11] 4,406,622
[45] Sep. 27, 1983

[54] REMOVABLE ATTACHMENT FOR PARTIAL DENTURE

[76] Inventor: Han S. Yoon, c/o H. S. Yoon's Dental Clinic, Rm. No. 202, #156, Insa-dong, Chongro-ku, Seoul 110, Rep. of Korea

[21] Appl. No.: 392,808

[22] Filed: Jun. 28, 1982

[30] Foreign Application Priority Data

Jan. 8, 1982 [KR] Rep. of Korea .................. 87/82

[51] Int. Cl.³ ............................................. A61C 12/22
[52] U.S. Cl. .................................. 433/172; 433/177
[58] Field of Search ............ 433/172, 177, 178, 182, 433/183, 191

[56] References Cited

U.S. PATENT DOCUMENTS

| | | | |
|---|---|---|---|
| 1,664,433 | 4/1928 | Seabrook | 433/182 |
| 1,825,593 | 9/1931 | Kempf | 433/208 |
| 1,976,085 | 10/1934 | Neurohv | 433/177 |
| 2,545,316 | 3/1951 | Stark et al. | 433/177 |
| 2,835,034 | 5/1958 | Plotnick | 433/178 |
| 3,427,718 | 2/1969 | Scott | 433/182 |
| 3,429,043 | 2/1969 | Androus et al. | 433/183 |
| 3,672,057 | 6/1972 | Mays | 433/172 |
| 3,717,931 | 2/1973 | Konig | 433/177 |
| 4,302,187 | 11/1981 | Yoon | 433/177 |

*Primary Examiner*—Robert Peshock
*Attorney, Agent, or Firm*—Scully, Scott, Murphy & Presser

[57] ABSTRACT

The present invention provides a removable attachment for a partial denture having assembly with body member which is to be the connector body therein and a slider member. The assembly is provided with the body member including a slot having a relatively wide and a relatively narrow slot or recess, in which a corresponding portion of slider member can be slid, and a neck portion of slot, which has a major axis which is horizontal and at a right angle to the row of teeth, a slider member including a lock rod and a protruding member suitable for being retained in a notch of the body member and has an aperture which may be engaged by the lock rod. The slider member is retained in position by two protruders of which both have the function as a rigid latch when the wearer or user masticates any foods and another function as a spring loaded rod when the user pushes out the slider member with his fingertip, and of which one is integrally formed on the individual movable member having one surface corresponding to a portion of the mastication surface of a natural tooth, and the other one is fixed to said individual movable member by a suitable method, for example, such as welding, soldering and etc. and is spring-loaded about the body of the slider member, and by the hemisphere detents to receive two protruders.

12 Claims, 17 Drawing Figures

REMOVABLE ATTACHMENT FOR PARTIAL DENTURE

PRIOR ART STATEMENT

As a means of complying with the duty to disclose set forth in 37 C.F.R. Section 1.56, the applicant submits this Prior art statement and states that the art listed herein includes, in the opinion of the applicant, the closest prior art of which the applicant is aware.

1. U.S. Pat. No. 4,302,187, attachment for removably supporting a partial denture with a sliding locking assembly to an adjacent crowned natural tooth. The patent discloses an attachment for removably supporting a partial denture to an adjacent crowned natural tooth, including a sliding locking member which can be slid on the recess in the support member in the direction of horizontal and at a right angle to the row of teeth and also which has a locking rod for locking the partial denture with the protruder formed to the crown of the adjacent tooth, and a support member having the recess and a shaft for passing the lock rod which is integrally formed with the sliding locking member.

2. U.S. Pat. No. 3,672,057. attachment for removably supporting a partial denture to an adjacent natural tooth. The patent discloses an attachment for removably supporting a partial denture affixed to a natural tooth including a flat having a pinhole therein and a locking bar having an extending pin portion of a diameter to be received by the gudgeon member pinhole.

3. U.S. Pat. No. 1,976,085. dental restoration. The patent discloses dental restoration having female rests in which the pulpal walls diverge relative to each other from the bases of the rests, and a bridgework having male rests insertable into said female rests.

4. Swiss Pat. No. 424,085. Dispositif d'ancrage pour l'art dentaire. The patent discloses a dental anchor having a generally triangular cross-section and a second section having a generally triangular groove to receive the projecter of the first member. When the two members are mated together they can be secured by inserting a pin through a hole in the second member to be disposed against the first member.

5. U.S. Pat. No. 1,664,433. dental device. The patent discloses a combination of denture provided with a mortise and with a slot, and a plunger carried by said denture and slidably mounted therin in order to be thrust into said mortise, and a second denture provided with a tenon for detachably fitting into the mortise in order to hold two dentures together.

6. U.S. Pat. No. 3,717,931. anchor for dental prosthesis. The patent discloses an anchor comprising a tubular housing adapted to be threadably received into a tapped opening in a pseudo-tooth, forming a part of a dental prosthesis.

7. U.S. Pat. No. 2,545,316. dental attachment for use in connection with removable bridges. The application discloses a dental attachment for use in connection with removable bridges including a male element and a female element shaped for slidably engaging each other in a vertical direction about the axis of teeth. A locking pin is inserted at a notch portion of the male element, and the female element is provided with a locking member arranged for interlocking engagement with the portion of locking pin protruding when the male and female elements are in proper engaging position.

8. German Offenlegungsschrift Nr. 2427888, Kraftbrechendes Verbindungsgelenk für eine Freiendzahnprothese (Strongly-breaking joint for freeend dental prosthesis). This one discloses male and female jointmoulds. The mould has a base part and a joint part with a continuous transverse drilling for taking up a joint pivot. The base plate is shaped for fixing to a wax extension, which may be imbedded in a wax model for the masticutory plate of the dental prosthesis.

9. U.S. Pat. No. 3,427,718. dental prosthetic appliance connecting apparatus. This patent disclosures a connecting apparatus for dental prosthetic appliance comprising the combination of a body having an tilted peripheral side wall, and a number of parallel passages extending through the body from end to end thereof; and a cap having a socket therein and slot outwardly therefrom. A plurality of parallel pins are secured in the socket, one for and positioned to fit into each of the passages.

10. U.S. Pat. No. 3,429,043. Dental Bridge. This patent discloses a dental bridge for positioning one or more pontics in the mouth, the bridges including a bar carried by at least one abutment adjoining the area to be bridged and a sleeve which is adapted to frictionally embrace the bar, the pontics being carried by the sleeve formed of the type that are longitudinally curvilinear.

BACKGROUND OF THE INVENTION

1. Field of the Invention

The present invention generally relates to the removable attachment of Partial denture which can be fabricated as a sliding and locking attachment and in particular relates to the removable attachment including at least one protruder both having a function as a rigid latch when the wearer masticates any foods and another function as a spring loaded rod when the user pushes out the slider by his fingertip for clearing the attachment used. 2. Description of the Prior Art In the prior art, there are a variety of removable attachments for partial dentures. For example, Chayes type attachment (developed in U.S.A.), Ceka-anchor attachment (developed in Belgium) and Inoue type attachment (developed in Japan). Such three attachments have common characteristics in their construction but also have common defects.

Nevertheless they are troublesome to remove, after every mealtime. For cleaning by water, they must frequently be removed from the oral inside to the oral outside. Further, they are easily damaged by the mechanical shock inflicted on the abutment teeth they are connected to. In light of the physiology, when the repeated mechanical shock, generated when removing those attachments, are directly and greatly inflicted upon hte abutment natural tooth, it affects the abutment tooth of the user as a fatal blow. In other words, the repeated mechanical shocks will cause the root of the abutment natural tooth to be shortened and then cause the periodontal tissue of the abutment tooth to be loaded excessively. Hence, the excessively loaded shock to the abutment teeth can cause the periodontal tissue to become inflamed. They can only be operated on with special instruments which are normally expensive.

In spite of using the special instruments, according to the condition of the natural teeth of the patient, it is often impossible to administer medicine to the patient, and even if the patient displays a normal condition of natural teeth, it is very difficult to administer medicine to the patient, because the surgical procedure requires a high degree of precision. Although, they practice with high precision on the patient, a sudden separation of a loosened partial denture can occur when even small amounts of wear or loosening of the attachment has occurred.

Further, the prior art attachments have a common and prime shortcoming apparent upon its removal in a vertical direction about the row of teeth or occlusal surface of teeth. That is, if the wearer masticates foods with adhesive characteristics, such as gum, caramel, hard candy, taffy, jelly beans, marshmellow and etc., those attachments can be easily removed, even if, the user or wearer never intended to remove the attachment. This is due to said removal in the vertical direction because the movement of the vertical force is usually generated during masticating foods having adhesive feature.

For all that, if any device is provided within those attachments for preventing the vertical movement, mechanical shock can be directly inflicted on the abutment natural tooth due to the construction feature thereof, and which causes the root of the abutment tooth to be shortened and the periodontal tissue to become inflamed.

One of the prior arts is provided within U.S. Pat. No. 4,302,187 issued on Nov. 24, 1981 which is my invention and is a parent invention relative to this application. There is described a removable attachment for a partial denture without the mentioned blemishes hereinbefore. The attachment, as described in the above U.S. Pat. No. 4,302,187, is characterized in that the direction of the movement of the slider member is horizontal instead of vertical as in the prior art, and a protruder attached to a crowned abutment natural tooth has a minimum length for avoiding the mechanical shock generated when removing itself, and which is provided for connecting the abutment tooth to the attachment by a slider and in that, the attachment can be manufactured and hence minimize the cost. Further the attachment can be installed without the need for specialized instruments but with high mechanical precision. However, in light of the general phenomenon of mastication that is, vertical force primarily generated during mastication and also secondly, the lateral movement generated during mastication, there is a disadvantage that if the wearer masticates foods with strong adhesive features or characteristics of relatively low softness and relatively high hardness, the slider member of the above mentioned attachment can be, sometimes, slid in the lateral direction. Also, there is provided the protruder having a minimum length for preventing the mechanical shock generated when removing the attachment. However, I have found that there is another phenomenon, that is, another shock should be generated when masticating foods. The later shock is generated due to the difference between length of possible movement of tooth and gingiva. According to a theory in the dental field, it is acceptable to rock the tooth by 0.08 mm–0.21 mm as a positive reaction and the gingiva by 0.27 mm–0.38 mm as a positive reaction. As suggested in the above range of data, the movement of teeth and gingiva are needed for maintaining the given lifes thereof. However, the excessive movements thereof over that of the above mentioned ranges of movement are represented to reduce or destroy the given lifes of the tissue and the root of the tooth as the negative reaction. However, the attachment of Patent 4,302,187 is without a device for preventing these kind of shocks.

Also, in the above mentioned patent 4,302,187, when the average height of teeth is lowered, the retaining force of the attachment in the locked (stable) position is weakened due to the constructive shape thereof. For avoiding this defect, the model of the attachment should be distinguished by two types, that is, one type is applied to wearer when the average height of teeth is either normal or high and the other type is when the average thereof is low. Further, in the case of the older permanent teeth, that is, of the physiologically very worn teeth, there is a disadvantage that the attachment of Patent 4,302,187 can not be applied to wearer. For effectively meeting the phenomenon of the occlusal surface, the occlusal surface of maxillary teeth must be matched with that of the corresponding mandible teeth. However, even if the occlusal surfaces are matched substantially to each other, when the teeth are very worn and in particular, the used attachment of maxillary teeth is matched unfortunately with the attachment of the corresponding mandible tooth, the attachment can be slid in the lateral direction by the combined force in the downwardly inclined and lateral direction generated when masticating foods. Once the above-mentioned sliding of the attachment occurs from the stable or locking position thereof, the wearer cannot masticate any more.

When the missing tooth is, for example, a tooth between the bicuspid and molar, the technique of the fixed bridge is generally applied thereto. The bridge is generally distinguished by two kinds thereof, that is, one is a fixed bridge and the other one is a removable bridge, but the latter one is closer to the classification of the partial denture. Also, in the fixed bridge field, it is generally known that a pontic corresponding to the missing tooth is connected between the abutment natural teeth so as to minimize the contacting portion of pontic to the surface of gingiva. The minimal contacted portion of pontic with the surface of the gingiva causes an embrasure to be greatly created between the pontic and the gingiva as well as the abutment natural teeth. The great embrasure is an extra shape which does not appear in the natural oral. Hence, the wearer having the great embrasure in his oral is indisposed or inconvenienced with the embrasure. But in light of oral physiology, the great embrasure does not have bad effects on oral health because there is provided a massage effect of gingiva by passing a piece of the foods through the embrasure. However, in accordance with the old habit of no embrasure or small embrasure of wearer, he requests often that the dentist blocks his embrasure so that food may not pass through. If the embrasure is to be blocked, the portion of the pontic contacting to the gingiva must be broadened. However, the broadened contacting portion thereof causes easily the portion of gingiva under the broadened portion to be inflamed, so that, for treating the inflamed portion the fixed bridge must be removed from the fixed position, where the inflammation resulted from the storage of a secretion of the tissue and a leftover foods under the broadened portion of the pontic. Also, in light of the mechanism of the fixed bridge, as the pontic connected between the abutment teeth is maintained in the lifting position from the gingiva, when masticating the foods, the masticating force is applied to the occlusal surface of the pontic like to the occlusal surface of the natural tooth. The force applied to the pontic is distributed to both abutment teeth while the pontic is never supported by gingiva. Thus, the pressure owning to the masticating force is transfered to the both abutment tooth from the center point of the occlusal surface of the pontic, in the inclined direction from the central point. Of course, during this time, the excessively loaded shock is applied to the abutment natural teeth.

For this case, Plotnick's attachment (U.S. Pat. No. 2,835,034) of the prior arts can be considered usable, but in the Plotnick's attachment, the pressure owing to the mastication is, also, applied to the rest of the attachment and hence applied to both abutment teeth in the same way with the above fixed bridge case. Lastly, the Plotnick's attachment cannot be used to replace the fixed bridge therewith so as to prevent the defects from the fixed bridge. Further, the removal direction from the locked position of the Plotnick's attachment is vertical, so that the attachment can be removed suddenly when masticating foods having adhesive features.

It is therefore an object of the present invention to provide a removable attachment for a partial denture which can be used in a variety of applications including cases where the deformation of the remaining natural teeth is provided for anyway and where the abutment teeth are few in number or somewhat damaged.

It is a further object of the present invention to provide a removable attachment for a partial denture which can be used for avoiding the above mentioned shortcomings from the fixed bridge.

It is another object of the instant invention to provide a removable attachment for a partial denture, which can overcome the defects from the prior arts such as U.S. Pat. 4,302,187.

It is yet another object to the present invention to provide a removable attachment for a partial denture, which can be safely used and which include an individual movable member having at least one protruder with both the function as a rigid latch when the wearer mastificates foods and a function as a spring loaded rod when the wearer pushes out the slider with his fingertip in the lateral direction.

It is a further object of the present invention to provide a removal attachment for a partial denture, which can be sticked substantially, against the lateral movement of when strongly masticating foods, the slider fast to the body.

It is an object of the present invention to provide a removable attachment for an partial denture where the shock in the vertical direction, generated when masticating foods and by the difference span between length of possible movement of tooth and gingiva when an artificial tooth was used for the missing tooth, is not directly applied to the roots and the periodontal tissue of the abutment natural tooth.

It is still another object of the present invention to provide a removable attachment for a partial denture which is a unity type and which can be used with the impertinence relation to the anatomical condition of the teeth of the patient.

In accordance with the aspects of the present invention, there is provided the individual movable member which is mounted into the slider, which has at least one protruder extended through at least one hole formed with the bottom portion of slider to the outside thereof for reflecting the view point which in the general attachment for a partial denture, the stability and retaining force of the attachment are of prime importance, where the individual movable member can be moved individually with the slider and also has a upper surface therof, almost covering the upper surface of the slider as an occlusal surface of natural tooth.

SUMMARY OF THE INVENTION

The present invention relates to a removable attachment of a partial denture with a lockable slider assembly having an individual movable member and a body member being the connector body. This invention includes a relatively wide slot and a narrower slot or sliding recess so that from a sectional view it is nearly horizontal and is at a right angle to the major axis of the teeth, as well as at least one protruder intergrally formed to the bottom of the individual movable member. At least one recess of the hemispherial type is formed on the upper surface of the sliding slot of the body member for receiving the protruder of the individual movable member. The slider member is retained in a locked position by the use of the protruder and the recess of the hemispherial type so that it will not move to an unlocked position while food is being masticated. The slider is also provided with a slot for receiving the individual movable member and a hole for passing the protruder integrally formed with the bottom of the individual movable member therethrough so that the slider member may be moved between a locked and unlocked position but will not be totally removed from the body member. The individual movable member is also provided with a spring-loaded rod so that the individual movable member may move in the vertical direction within certain bounds but will not be totally removed from the slider.

The present invention may be used with a partial denture when only the cuspids are present and in distal extension protheses when bilateral and/or unilateral teeth are missing as well as when one of the molars is missing. It may be easily dismensioned to accommodate dental features of various sizes and heights and may be operated with dental instruments commonly in use.

It is secured by a mechanical connection: a rod and oval aperture rather then being in direct contact with the abutment teeth and is fabricated from relatively low cost materials. Finally, it may be used where the height of the crown of the abutment natural tooth or the adjacent tooth is above at least 2.9 millimeters, a condition often encountered when teeth are used for a lengthy period of time.

Other detailed features and advantages of the instant invention will become apparent from the accompanying drawings taken in conjunction with the detailed description of the presently preferred embodiments of the invention.

DETAILED DESCRIPTION OF THE INVENTION

Figure 1:
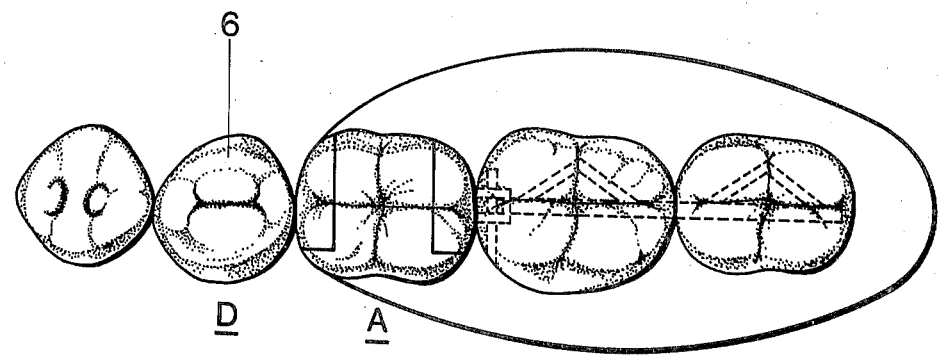
FIG. 1 is a plan view of an embodiment of the prior art.
Figure 2:
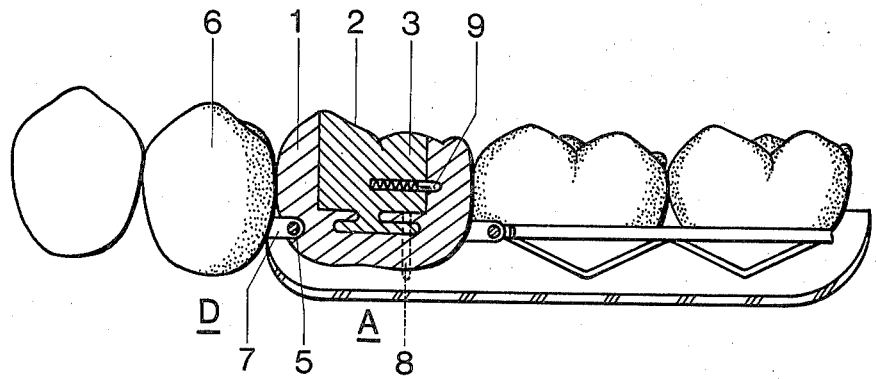
FIG. 2 is a sectional view of an embodiment of the prior art.
Figure 3:
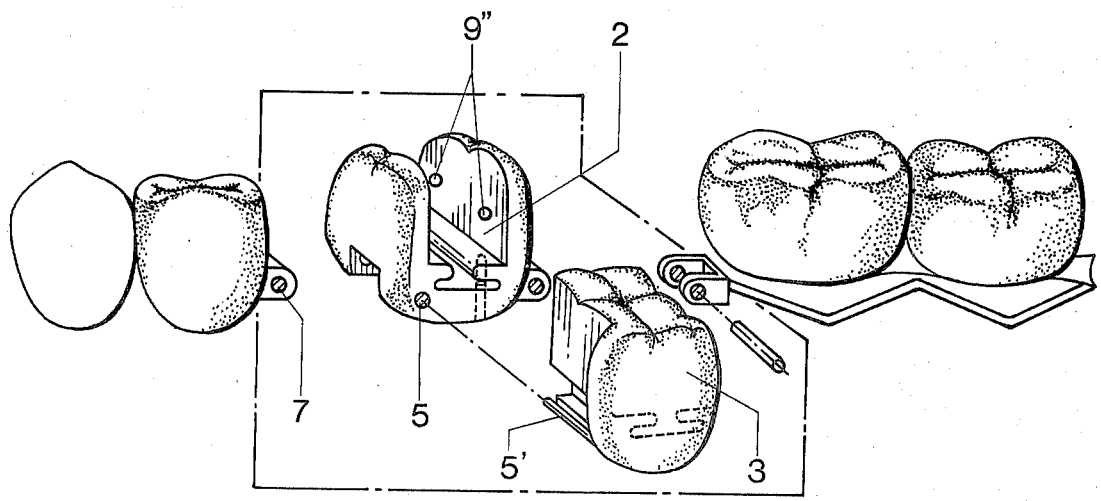
FIG. 3 is an exploded perspective view of an embodiment of the prior art.

Referring to FIGS. 1, 2 and 3, the structure of an attachment according to the prior art is shown. The body member 1 of attachment(A) for mounting the partial denture into the oral side is provided with a relatively wide and narrow slot or recess 2. The recess 2 has a cross-section form so that it is substantially horizontal and therefore at a right angle to the major axis of teeth. As shown in detail in FIG. 2 or 3 a slider member 3 has a surface in the form of tooth and is provided with an extending "⊥" type portion. The slider member 3 rides in recess 2 and also an extending portion of slider rides in recess to prevent the slider member 3 from being displaced upwardly from the body 1. The slider member 3 may be moved lingually or buccally by simply pushing it with a fingertip. The body 1 includes a notch 4 and aperture 5 which receive the lock rod 5' mounted on the slider member. The abutment natural tooth D is provided with an artificial crown 6 having a protruder 7 which also has a shaft to receive the pin 5'. Therefore, the connection of attachment A of the partial denture to the abutment tooth D can be accomplished by positioning the body so that the protruder on crown 6 of abutment tooth D is inserted into the notch 4 of body 1. Then slider member 3 is moved so that the lock rod 5' slides through the aperture 5 and into the shaft of the protruder 7. The sliding portion of slider member 3 has a certain slot at one side thereof so as to allow the slider member 3 to slide over a limited range within the body 1.

The slider member 3 is retained in its porition corresponding to a locked or unlocked condition by the use of a spring-loaded lock pin 9 and two detents 9".

However, there is provided a limitation to the position of the spring-loaded lock pin 9 because the lock pin 9 is positioned on the side wall of the slider member 3. Thus, if the teeth are very worn, that is, the height of the crown of the teeth is below than 4.0 mm, the attachment can not be used due to the lack of space for fabricating the spring-loaded lock pin. Further, if the occusal surface of teeth is not horizontal but an inclined surface, the attachment can be slid unfortunately when masticating foods.

Figure 8:
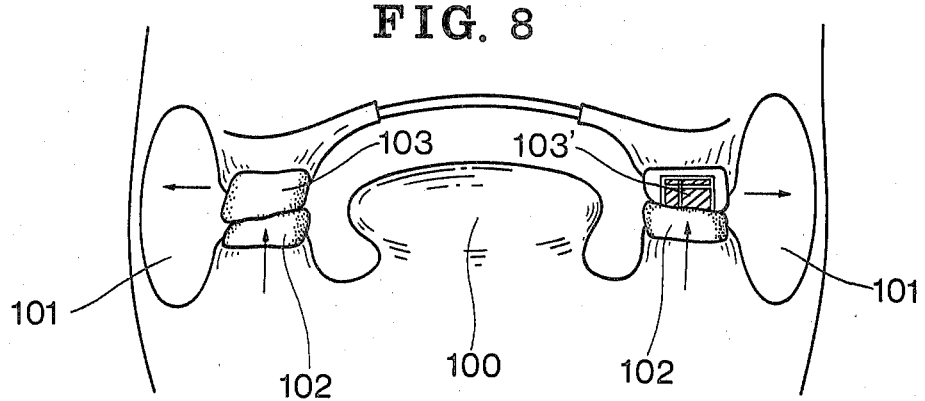
FIG. 8 is a sectional view of the oral in which the teeth are very worn.

This condition is more detailly shown in FIG. 8. In FIG. 8, there is shown a cross-sectional view of the oral cavity, in which the teeth are very worn. A tongue is marked by the reference number 100, and the cavity between teeth and cheek is shown exaggerated from the normal condition, reference number 101. Number 103 indicates a maxillary tooth while Number 103' designates the attachment mounted on the maxillary gingiva. It is understood from the drawing that the worn type of the teeth designates the direction of the downward tilt. In addition, the worn type thereof is generally created by overall worn teeth. Hence, the mastication with this condition causes the attachment to be slided laterally.

Figure 4:
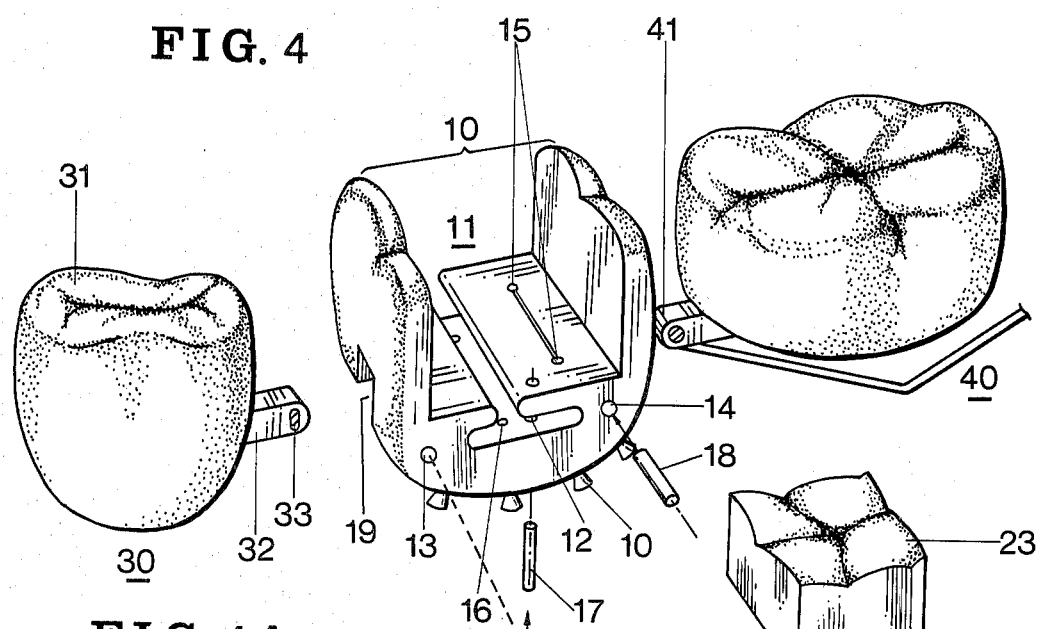
FIG. 4 is an exploded perspective view of an embodiment of the instant invention.
Figure 4A:
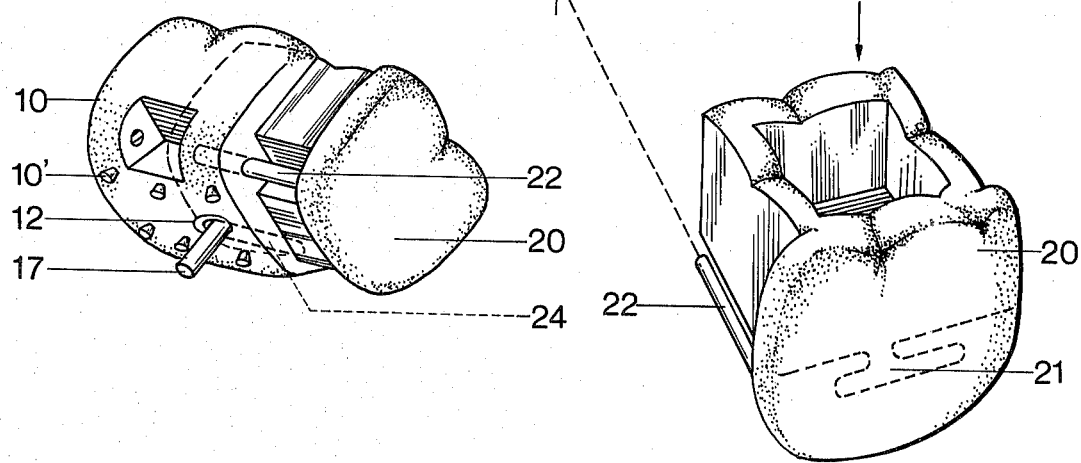
FIG. 4A is a perspective view of an embodiment of the present invention, which is depicted at the bottom side.

In FIG. 4, a preferred embodiment according to the present invention includes a body member 10 and slider member 20. A body member 10 includes a slot 11 having a relatively large cavity (First Cavity), a relatively small cavity (Second Cavity) and a neck portion connecting first cavity to second cavity. The first hemispherial detents 15 provided on the bottom of the first cavity and second hemispherial detents 16 is formed on the bottom of the second cavity. Also, the body member is provided with the first notch 19 for receiving the first protruder 32 formed on the lowest position of the artifical crown 31 which is covered by the adjacent abutment natural tooth 30 and with the second notch 19' for receiving the second protruder 41 formed on the artifical tooth and frame 40. The body member 10 is provided with the first aperture 13 for receiving the lock rod 22 of slider member and with the second aperture 14 for receiving the connecting pin, so that the body member 10 or attachment assembly is retained between the abutment tooth 30 and the artifical tooth or frame 40. As can best be seen in FIG. 5A, the sliding portion 21 of the slider member 20 has a guide slot 24 formed in one of its side portion. This slot 24 is provided to allow the slider member 20 to slide over a limited range within the body member 10. During assembly the slider member 20 is inserted into the body member 10 and the limiting rod 17 is inserted through the shaft 12 and the slot 24 and hence is permanently affixed there. Further, as can best be seen in FIG. 4A, the bottom surface of the body member 10 is provided with a plurality of the small protruder 10' which have respectively, a shape of reversed triangular section.

Figure 5A:
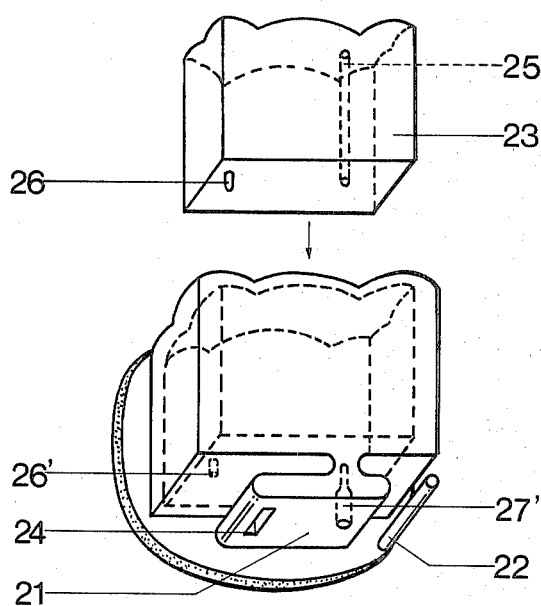
FIG. 5A is an exploded perspective view of slider member of the instant invention.

FIG. 5A shows an exploded perspective view of a slider member 20 according to the instant invention. In FIG. 5A, a slider member 20 is provided with a chamber for receiving the individual movable member 23. The individual movable member 23 is retained in its position corresponding to a locked and unlocked condition or a moving condition by the use of a fixed pin 26, and a second fixed pin 27 which is spring-loaded and the first and second hemisphere detents so that an individual movable member 23 can not be easily removed from the slider member 20. Both tips of the first and second fixed pins are fitted with the first and second hemisphere detents so as to ensure positioning of the slider member 20 at the locked and the unlocked positions within a limited range. As the first and second fixed pins are fitted with the first and second detents in a vertical direction which almost coincides with that of the vertical force generated when masticating foods, when the slider is in the locked position, the masticating force loaded into the attachment almost loads to the surface of the individual movable member 23, where the surface of the member 23 extends over the occusal surface of the attachment. Hence, the stronger masticating force may cause the stronger fitted force to be created in the slider through connection between the first and second fixed pins 26, 27 and the corresponding detents. Finally, the slider member 20 can not slip from the locked position to the unlocked position when masticating foods.

Figure 5B:
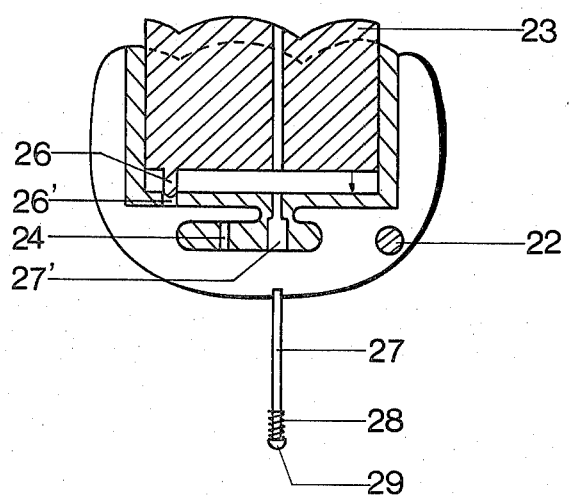
FIGS. 5B–5D depict respectively the assembling steps of the slider according to the instant invention.
Figure 5C:
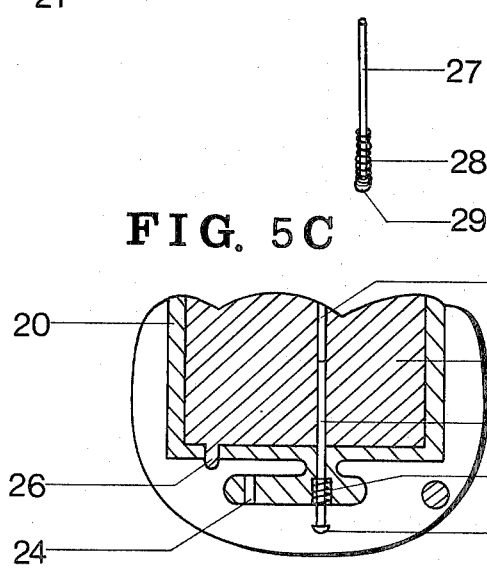
Figure 5D:
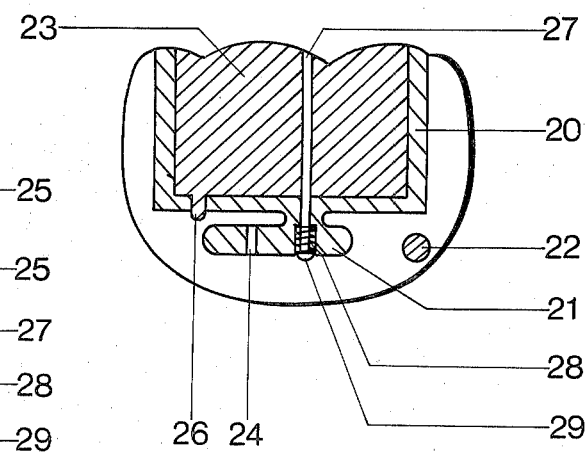

FIGS. 5B-5D show how the individual movable member 23 is assembled into the slider member 20 by usage of the 2nd fixed spring-loaded pin 27. In FIG. 5D, the slider member 20 is completed with the individual movable member 23 by the second fixed pin 27. In the same drawing, it is shown that the heads of the 1st and 2nd fixed pins are slightly extended to the outside of the bottom of the slider 20 through the corresponding slots 26' and 27', respectively. Also, FIG. 5D shows that the other end of the 2nd fixed pin is matched with the occusal surface of the slider 20 being an artificial tooth.

Figure 6A:
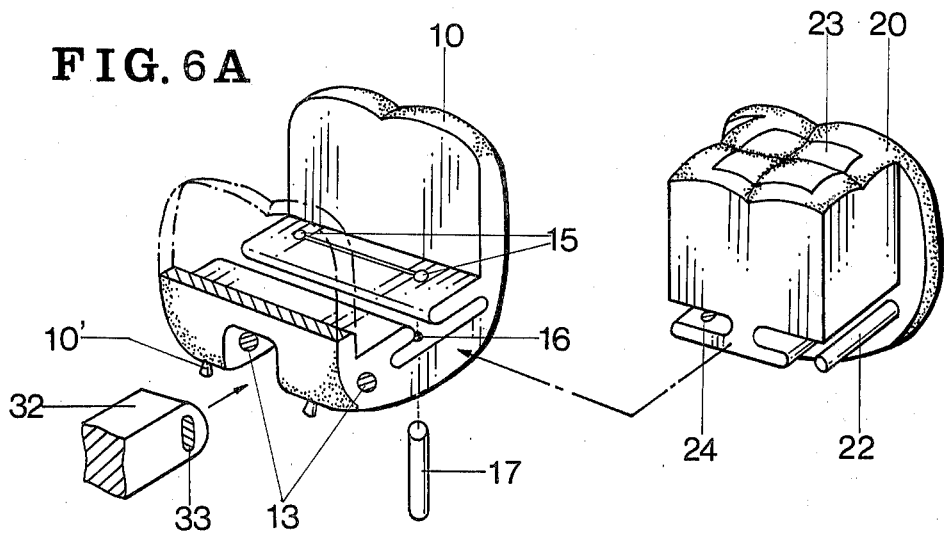
FIG. 6A is a partial exploded perspective view of an embodiment of the instant invention.

As can best be seen in FIG. 6A, the slider 20 can be assembled with body member 10, so that the first protruder 32 is connected with the attachment assembly. In the same drawings, the first protruder 32 is provided with an oval aperture 33 so as to insure a limited movement for compensating the differential span between lengths of possible movement of tooth and gingiva. In other words, the lengthy diameter $d_1$ of the oval aperture 33 as referred to in FIG. 6D, is longer for example as $d_2$ than the diameter $d_4$ of aperture 13. This relationship can be represented by the following equation:

$$d_2 = d_1 - d_4 = d_3$$

Please note that, of course, the span $d_2$ and $d_3$ may be a differential span between lengths of positive possible movement of tooth and gingiva.

Figure 6B:
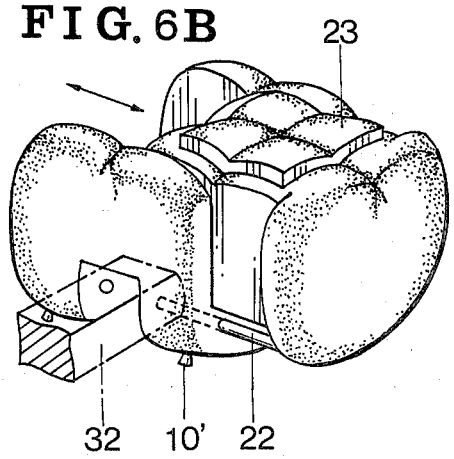
FIG. 6B depicts the condition of an embodiment when the slider moves from the unlocking position to locking position along sliding recess.
Figure 6C:
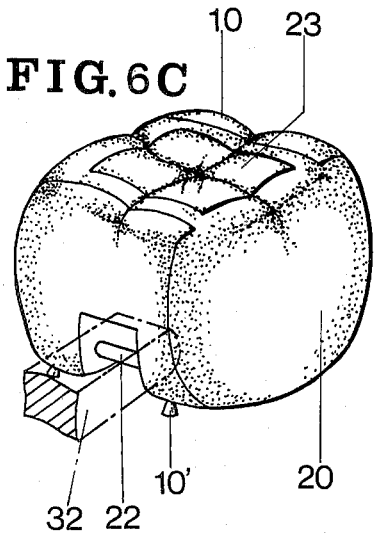
FIG. 6C depicts a condition of an embodiment when the slider stopped with its locking position.
Figure 6D:
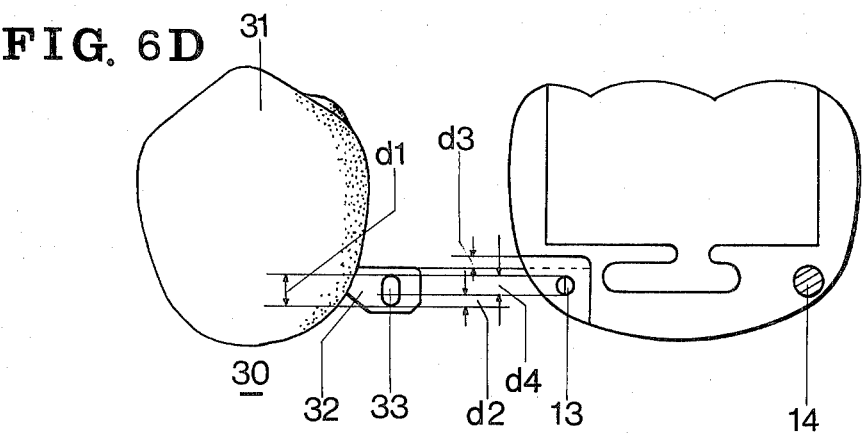
FIG. 6D depicts, in an embodiment according to the present invention, a construction for buffering the shock generated when masticating foods.

In FIG. 6B, it is shown that the individual movable member 23 somewhat protrudes in the upward direction from the matching surface of the occusal surface of slider member 20. That is, the individual movable member 23 in FIG. 6B, is positioned between the locked and unlocked positions thereof or between both stable positions of the slider member 20. Further, slider member 20 is moved more in the direction of the left in the drawing, thereby positioned in the stable position. One stable status of the slider member 20 is best seen in FIG. 6C. In FIG. 6C, it is illustrated that an upper surface of the individual movable member 23 is matched with the occusal surface of the slider member 20 and further with the upper surfaces of the body member 10. From the above facts, it is understood that the status of the individual movable member 23 can be illustrated by the three positions, which are matched position, unmatched position or in the moving position. When the individual movable member 23 is in the matched position, it means that a slider member 20 is completely inserted into or removed from the body member 10, so that the first protruder 32 formed on the artificial tooth or abutment tooth 30 is either retained or not in the first notch 19 by the lock rod 22 passing through the oval aperture 33 of the first member 32, thereby resulting in the whole assemble or partial denture to be secured to the abutment tooth or to be free from the abutment tooth. When the individual movable member 23 is in the unmatched position, it means that the slider member 20 is in a sliding status to one of either described locked positions.

Figure 7A:
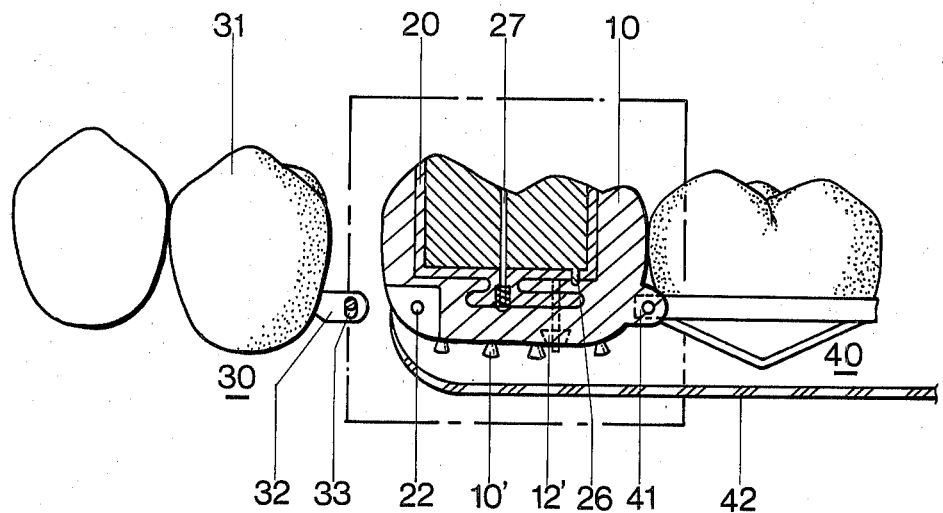
FIG. 7A is a sectional view of a part of the embodiment according to the instant invention, of which a part includes a buffer construction.

FIG. 7A shows an alternate arrangement of the 2nd protruder 41 and a plurality of small protruders 10' which are to be used when the tight and rigid coupling between the body member 10 and the resin base 42 is needed. Also it is illustrated that the body member 10 is provided with a slot of the reverse trapezoid type which is to be used when the tight and rigid coupling between the body member 10 and the limiting rod 17 and the resin base 42 is needed.

Figure 9:
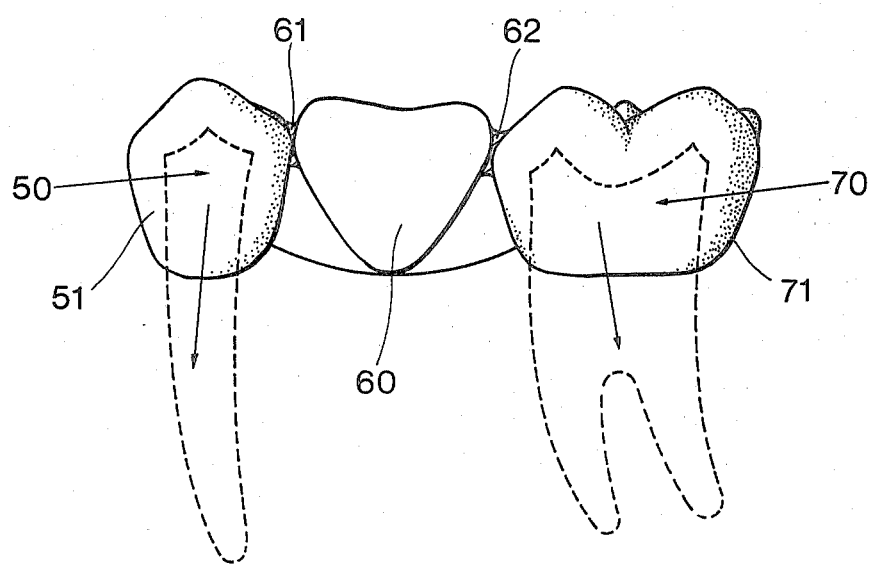
FIG. 9 is a perspective view of the fixed bridge of the prior art.
Figure 7B:
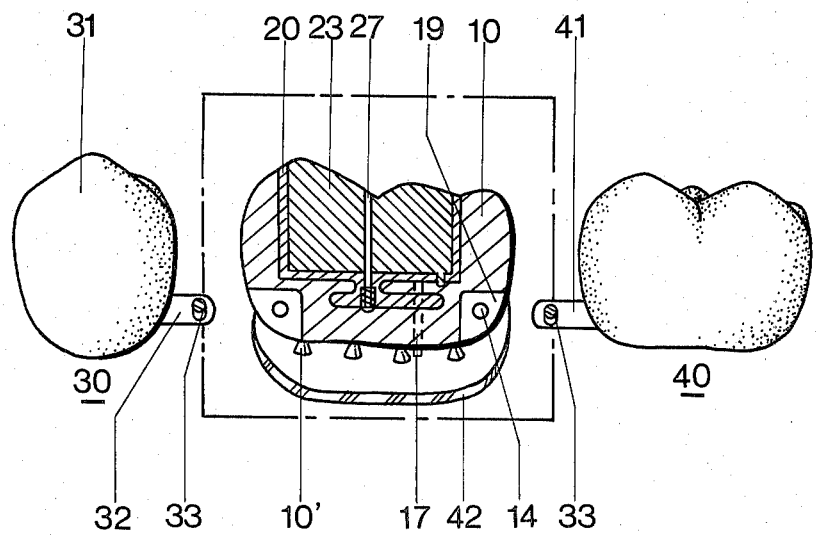
FIG. 7B is a perspective view of when an embodiment according to the invention is utilized instead of the fixed bridge and includes a buffer construction.

Referring FIG. 7B, an other embodiment shown according to the present invention, can be utilized instead of the conventional bridge. In this case, the body member 10 is provided with at least a small protruder 10' for causing the rigid and tight coupling to be provided between the body member 10 and the resin base 42. In FIG. 9, a conventional bridge is perspectively shown with a pontic mounted between Crown 51 formed on the first abutment tooth 50 and Crown 71 formed on the second abutment tooth 70, and fixedly connected between both said Crown 51 and 71 by coupling portions 61 and 62. In FIG. 9, it is best seen that a pontic 60 is not supported by the gingiva and also the great embrasure is provided around the gingiva under the pontic 60.

Therefore, according to the other embodiment in FIG. 7B, the mentioned great embrasure can be eliminated thereby removing the above mentioned shortcomings from the conventional.

As illustrated on the above embodiments, an alternative to the use of a lingual bar in cases of unilateral defects is to support the partial denture by a telescopic crown. Particularly, a telescopic crown is useful when teeth between the canine and rearmost molar are missing. Further, a partial denture according to the invention is useful when teeth between the canine and rearmost molar and teeth of incisor are missing and when teeth of molars are missing.

Further the present invention may be used with a partial denture when only the canine teeth are present as well as when bilateral and/or unilateral teeth are missing.

In particular, the present invention is useful when the teeth are very worn and/or when the average height of worn teeth is lowered by as much as 3.0 mm (0.12 inch).

While I have described my invention in some detail and in several embodiments, it will be apparent to those skilled in the art that various changes and modifications can be made without departing from the spirit of the invention. The invention should, therefore, not be limited by the description above but only by the claims which follow.

What is claimed is:

1. In an improved removable attachment for a partial denture comprising a slider member having a sliding portion and a lock rod and a body member including a slot for receiving said slider member, a limiting rod for limiting the sliding motion of said slider member within certain bounds and at least one notch for receiving a protruder formed on the crown of the adjacent tooth, said improvement comprising:
   an individual movable member moving individually in said slider member;
   at least one fixed pin integrally formed with said individual movable member;
   at least one slot formed on the bottom portion to protrude a head portion of said fixed pin therethrough;
   a spring mounted to said fixed pin to spring-load said individual movable member when said individual movable member is moving within said certain bounds; and
   said head portion of said fixed pin dimensioned to mutual act with said spring and said fixed pin,
   wherein a force, generated when the exposed surface of said individual movable member is occluded with that of the corresponding opposite tooth, causes the binding force and retaining force between said slider member and body member to ensure the lock position of said slider member in said body member.

2. The attachment according to claim 1, wherein the height of said protruder is shorter than the height of said notch formed on said body member, and the longitudinal dimension of the oval aperture formed on said protruder is larger than the dimension of said lock rod.

3. The attachment according to claim 1, wherein the slot of reverse trapezoid type is formed to the bottom portion of said body member so as to ensure a tight and rigid coupling between said limiting rod and the resin base.

4. The attachment according to claim 1, wherein said notch formed on said body member is a pair.

5. The attachment according to claim 4, wherein said notch on the body member is formed so as to minimize the span between said adjacent natural tooth and said body member, and the other side of said notch is provided with a protruder.

6. The attachment according to claim 4, wherein said resin base being the artificial gingiva is supported on the natural gingiva, and, an embrasure formed between teeth is prevented by said resin base.

7. The attachment according to claim 6, wherein at least one small protruder is provided within the bottom portion of said body member to ensure a tight and rigid coupling between said body member and said resin base.

8. The attachment according to claim 1, wherein said individual movable member is integrally provided with at least one said fixed pin and is fixedly provided with one other fixed pin.

9. The attachment according to claim 1, wherein only one fixed pin is provided on said individually movable member.

10. The attachment according to claim 8, wherein said another fixed pin comprises the head portion of an end and the rod portion of the other end to be fixed to said individual movable portion through the shaft therein.

11. The attachment according to claim 8 or claim 9, wherein, a surface exposed of said individual movable member in said slider member is matched with the exposed surface of said slider member as a natural tooth type.

12. The attachment according to claim 11, wherein at least a portion of said exposed surface of said individual movable member is occluded with the corresponding opposite tooth.

* * * * *